United States Patent [19]

Kern et al.

[11] Patent Number: 4,839,284

[45] Date of Patent: Jun. 13, 1989

[54] MURINE HOST-VECTOR SYSTEM CAPABLE OF AMPLIFYING AND EXPRESSING TRANSFECTED GENES

[75] Inventors: Francis G. Kern, Rutherford, N.J.; Claudio Basilico, New York, N.Y.

[73] Assignee: New York University, New York, N.Y.

[21] Appl. No.: 734,922

[22] Filed: May 16, 1985

[51] Int. Cl.$^4$ .................. C12P 21/00; C12N 15/00; C12N 5/00; C07H 15/12
[52] U.S. Cl. ........................... 435/68; 435/70; 435/172.3; 435/235; 435/240.2; 435/317.1; 435/320; 935/32; 935/43; 935/371; 935/60; 532/27
[58] Field of Search ............... 435/68, 70, 172.5, 235, 435/91, 243, 253, 317; 935/32, 43, 37, 60; 536/27

[56] References Cited

PUBLICATIONS

Subramani, S. et al., *Mol. Cell. Biol.* 1: 854–864, 1981.
Simosen, C. et al., *Proc. Nat. Acad. Sci. U.S.A.* 80: 2495–2499, 1983.
Mulligan, R. C. et al., *Science* 209: 1422–1427, 1980.
Pellegrini, S. et al., *Cell* 36: 943–949, 1984.
Daily, L. et al., *J. Virol,* 49: 984–987, 1984.
Southern, P. J. et al., *J. Mol. Appl. Genetics,* 1: 327–341, 1982.
Rio et al. (1985) *Science* 227:23–28.
Tyndall et al. (1981) *Nucleic Acids Res.* 9: 6231–6250.

*Primary Examiner*—Thomas G. Wiseman
*Assistant Examiner*—S. Seidman
*Attorney, Agent, or Firm*—Darby & Darby

[57] ABSTRACT

Disclosed herein is a method for amplifying and expressing transferred genes by temperature induction.

17 Claims, 4 Drawing Sheets

MURINE HOST-VECTOR SYSTEM CAPABLE OF AMPLIFYING AND EXPRESSING TRANSFECTED GENES

FIELD OF THE INVENTION

One aspect of this invention relates to a novel cell line useful as an expression system for transfected genes.

Another aspect of this invention relates to a method for amplifying genes transfected in a murine host cell by temperature induction.

BACKGROUND OF THE INVENTION

It is well-known to transfer cloned genes into host cells as a means for producing the proteins expressed by such genes. Numerous eukaryotic host/vector systems have been used to express cloned genes. In general, the goal of such systems is to amplify the copies of the cloned gene and thus increase the yield of the protein expressed by such gene.

One known system uses recombinant bacterial plasmids that can be propagated and expressed in mammalian cells that carry the origin of DNA replication and transcriptional regulatory elements derived from the genome of simian virus (SV-40). See R. C. Mulligan and P. Berg, Science, 209:14–22 (1980); S. Subramami, R. C. Mulligan, P. Berg, Mol. Cell. Biol. 1, 854 (1981), P. J. Southern and P. Berg, 1:327 (1982); C. C. Simonson and A. D. Levinson; Proc. Nat'l Acad. Sci. USA, 80:2495 (1983). These vectors include the SV-40 T antigen gene. The expression of this gene is required to activate replication of the SV-40 origin in monkey cells.

Subsequently, it was discovered that the usefulness of these SV-40-derived vectors could be improved by using them with permissive cells (i.e. cells supporting the replication of the virus) carrying integrated copies of the T-antigen (Y. Gluzman Cell 23, 175 (1980)). The permissive cells, termed COS (CV1-origin SV-40), are able to support replication of any DNA that contains an intact SV-40 origin sequence. These COS cells express the early viral gene product, T antigen, and are able to support replication of any DNA that contains an intact SV-40 origin sequence. The drawback of this system is that the COS cell line constitutively expressed active T antigen. Thus, it was not possible to regulate replication of SV40 vectors.

Regulation of gene expression is desirable for several reasons. For example, if a transfected gene product is toxic to the host, it would be advantageous to regulate (and particularly to defer) expression of that product.

In addition, extrachromosomal gene replication can in itself be lethal to the host cell. Thus, it is advantageous to be able to defer the onset of replication until a critical mass of host cells can be prepared for efficient production of the desired protein.

In unregulated systems, it is difficult to select for stable transformants since large amounts of extrachromosomal DNA are continuously present. Also, since the clones expressing the gene of interest may die quickly because they carry on extrachromosomal replication, it is possible that such clones may be overgrown by clones that have lost the sequences of interest.

The present invention involves extrachromosomal gene amplification mediated by a temperature-sensitive large T antigen provided in trans in permissive mouse cells and takes advantage of the finding of that the polyoma late promoter can direct the expression of foreign coding sequences linked to such promoter.

The present invention involves a system for amplification and expression of transfected genes by temperature induction. The host cells comprise permissive murine cells that contain (and can express) a polyoma virus large T antigen gene whose activity can be regulated by temperature shift. The cells permit the expression of functional T antigen at a second temperature and restrict the function of this antigen at a first (higher) temperature. When cultured at the lower (permissive) temperature the cells produce a functional large T antigen. The functional large T antigen acts on a functional virus origin of replication also present in the host cell and causes replication and excision of an integrated plasmid. As a result, the number of copies of plasmid DNA present in the cell is increased on a logarithmic basis. The level of expression of the desired gene product is also logarithmically increased.

In order to express large quantities of large T antigen, the host cell is transformed to contain an integrated polyoma large T gene with a non-functional (or mutated) origin of replication to shut off replication of viral DNA and autoregulation of the large T gene.

The transformed cell is transfected with a vector containing a functional origin (of the same virus species as the large T antigen) the gene coding for the protein of interest (with proper control signals), and a dominant selectable marker.

In fact, transfection is not required. A vector can be inserted by microinjection or by infection of the host cell with a retroviral vector.

Selectable markers include neomycin resistance gene, guanine phosphoribosyl transferase and others.

The large T antigen produced in the resulting cell by virtue of the first transformation is available to act on the vector to cause replication of the vector DNA, including the gene for the protein of interest. This is why it is necessary for the vector to contain a functional origin of replication of the same viral species as the large T.

DETAILED DESCRIPTION OF THE INVENTION

Figure 1:
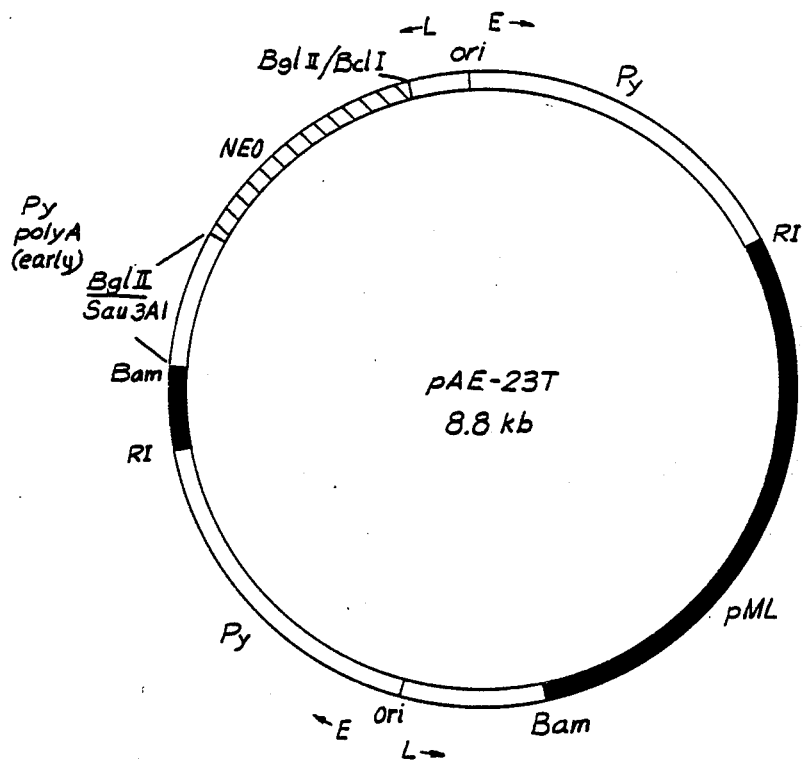

The parent cell line of the present invention was NIH-3T3, an immortalized mouse cell line of NIH Swiss origin available from the American Type Culture Collection, Rockville, Maryland.

Permissive NIH-3T3 cells were transformed with a plasmid, pB-32 containing a polyoma virus DNA molecule encoding a large T antigen gene and a polyoma replication origin deletion into the PML plasmid. The particular polyoma virus used was the temperature-sensitive (ts)-A strain. The origin was deleted by digestion with Bal-31 nuclease at the Bgl-1 site, which generated a deletion of nucleotides 5247-127. Other origin region deletions, however, would have been expected to impair the origin sufficiently to shut off replication and large T autoregulation.

Transfection of the cells was conducted by calcium phosphate precipitation according to the well-known method of Wigler, M. et al Proc. Nat'l Acad. Sci. USA, 76:1373, 1979.

All early proteins of ts-A strain polyoma virus are expressed in the thus transformed cells. The large T antigen is temperature-sensitive and the middle T antigen confers on the transformed cells the ability to grow on semisolid media (agar).

The transformed cells were, therefore, selected for ability to grow on agar and for ability to express temperature-sensitive large T antigen.

The latter ability was determined by indirect immunofluorescence assay, as follows:

Coverslips containing subconfluent cells were washed with Tris buffered saline, fixed with methanol:acetone (7:3), and dried. Rat antipolyoma tumor antiserum in Tris buffered saline (1:48 dilution) was spread onto the cells and the cells were incubated for 30 minutes at 37° C. The cells were washed with PBS and the bound antibody was detected with fluorescein labeled goat anti rat IgG.

Alternatively, the cells could have been transformed with a plasmid that coded for large T antigen alone. In that case, the cells would have been selected by cotransfection with a dominant selectable marker.

The important features of the plasmid are that it codes for large T antigen and that the polyoma origin of replication is deleted (or mutated) to shut off autoregulation of large T antigen and the replication and excision of the integrated large T-producing plasmid. Autoregulation is the binding of the large T antigen to the DNA sequences near the viral replication origin which in turn results in a shut off of large T antigen expression.

The ability of the clone to support the replication of an incoming plasmid that contains a replication origin can be tested to confirm that the T antigen is functional. This test can be conducted using Mbo I restriction endonuclease, which will only cleave newly replicated DNA.

The transformed cells make a functional large T antigen at 33° C. and a nonfunctional protein at 39° C. The cells should therefore be maintained at 39° C. until they are ready for use.

The transformed cells are preferably maintained in Dulbecco's Minimum Essential Medium (Gibco, Grand Island, N.Y.) containing 10% calf serum, and 500 units of penicillin and 0.1 g of streptomycin per liter. They should be maintained in an atmosphere containing 10% $CO_2$.

The transfection frequency of these cells is rather low. Therefore, selection of transfected clones made from these cells should be cautiously performed. Selection for neomycin resistance should be performed using low concentrations about 150-250 micrograms/ml) of G418 sulfate ("Geneticin" made by GIBCO, Grand Island, N.Y.) to avoid killing clones containing the transfected DNA.

The thus transformed cells are named WOP-32-4. They are on deposit at American Type Culture Collection, Rockville, Maryland under accession number CRL8806 (deposited on May 16, 1985). The cells of the present invention have been reported to express greater amounts of large T antigen than COP cells (a polyoma transformed mouse that is replication-negative—by origin deletion—but expression-positive) described by Tyndall, C. et al. *Nucl. Acid Res.* 9(23):6231 (1981). Moreover, the cells of the present invention express temperature-sensitive (thermolabile) large T antigen. Hence, they provide a useful temperature-regulated, amplification-capable, expression system for transfected genes and a useful host for recombinant gene expression.

The ability of the WOP-32-4 cells to amplify transfected genes was tested by amplification of the neomycin resistance gene and also of the chloramphenicol acetyl transferase (CAT) gene.

A plasmid was constructed containing neomycin coding sequences linked to the polyoma late promoter. (Suitable plasmids for this purpose must contain at least one functional polyoma origin.) The plasmid is depicted in FIG. 1. It does not contain complete large T coding sequences, but does contain two copies of the origin of replication (arranged in a partial tandem).

The plasmid of FIG. 1—named pAE-23T—was constructed in vitro. The gene for neomycin resistance was inserted at the Bcl-1 site at nucleotide 5021. The thus prepared plasmid was used to transfect WOP cells at 33° C. overnight. If a head-to-tail tandem plasmid is used, transfection can take place at 39° C. (for about 7 hours). The transfected cells were plated in 100 mm petri dishes ($2 \times 10^5$ cells/dish) and selected for neomycin resistance at 39° C.

Within 3-4 weeks, colonies were observed and maintained at 39° C. The colonies were picked and assayed for extrachromosomal viral DNA production using the method of Hirt, B. (1976), *J. Mol. Biol.* 26:365-369, after the cultures were shifted to the permissive temperature of 33° C. for 48-60 hours. Extrachromosomal DNA was detected by Southern blotting and hybridization to a nick-translated neo-resistance probe.

Briefly, the procedure used was as follows:

A solution containing 0.01 M Tris, pH 7.9, 0.01M EDTA, and 0.6% sodium dodecylsulfate was used to lyse cells. The cells in a 60 mm tissue culture dish were first rinsed with Tris buffer saline and then a 400-500 microliter sample of the SDS solution was placed over them. Lysis was allowed to take place; the cells were poured in an Eppendorf tube; 5M NaCl was added to a final concentration of 1M and the mixture was placed on ice over night. The mixture was centrifuged; the supernatant was saved, extracted with phenol/chloroform/isoamyl alcohol (25:24:1) and precipitated with ethanol. The pellet was resuspended in a small volume of Tris-EDTA (0.01M Tris; pH 7.9; 0.001M ethylene diamine tetraacetate). One half of the volume was subjected to agarose gel electrophoresis, the gel transferred onto nitrocellulose and hybridized with a NEO-specific probe.

Figure 2:
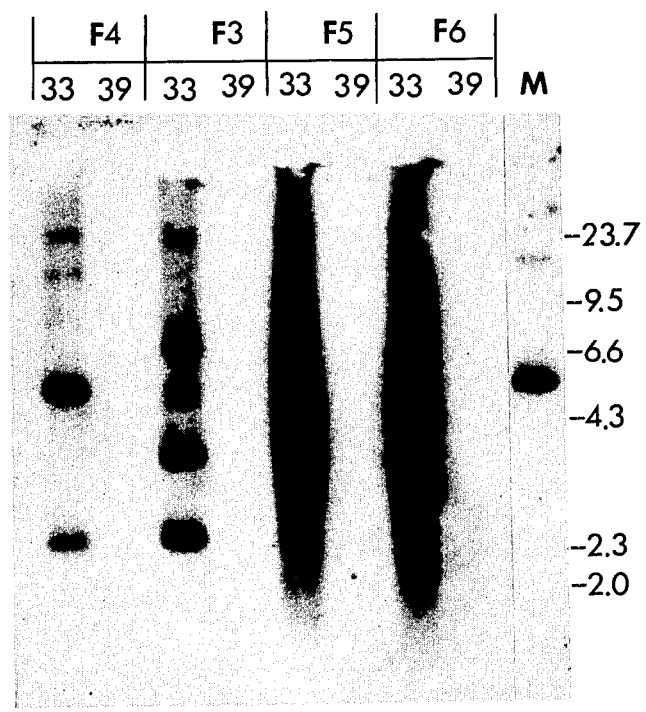

The results are shown in FIG. 2. FIG. 2 shows the free plasmid DNA obtained from four independent G418 resistant WOP-32 clones obtained by transfection with the pAE-23T plasmid (designated F3, F4, F5, F6). The numbers 33 and 39 above the gel lanes indicate growth at 33° C. and 39° C., respectively. M is the PAE-23T plasmid marker (forms I and II) hybridized to the same probe. The migration of DAN markers is indicated on the right margin (in kb). Four clones tested produced distinctly increased amounts of NEO-resistant DNA, either as discrete species of extrachromosomal DNA, as complete or deleted forms of the plasmid, or as a heterogeneous smear of extrachromosomal DNA. Two clones, F3 and F4, had segments corresponding in size to the tandemly repeated unit.

Figure 3:
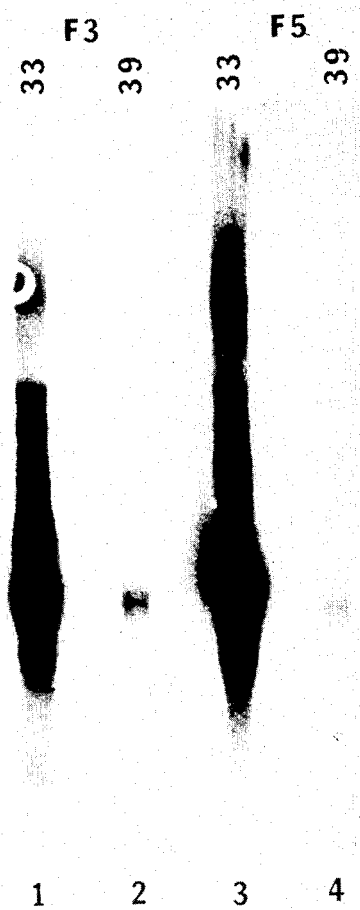

The extent of the proliferative responses varied. Two clones failed to proliferate. Another clone continued to proliferate for at least twelve days. Two clones produced a species of RNA corresponding in size to NEO-resistance RNA in amounts greatly amplified at 33° C. (compared to those produced at 39° C.). These are labeled F3 and F5 in FIG. 3, which is a Northern blot of micrograms of Poly A+ RNA from cells at either 33° C. or 39° C. hybridized to a NEO-specific probe. In FIG. 3, lane 1 is clone F3 grown at 33° C., lane 2 is clone F3 grown at 39° C., lane 3 is clone F5 grown at 33° C. and lane 4 is clone F5 grown at 39° C.

The above-described recombinant could not be easily assayed for extent of translation.

Figure 4:
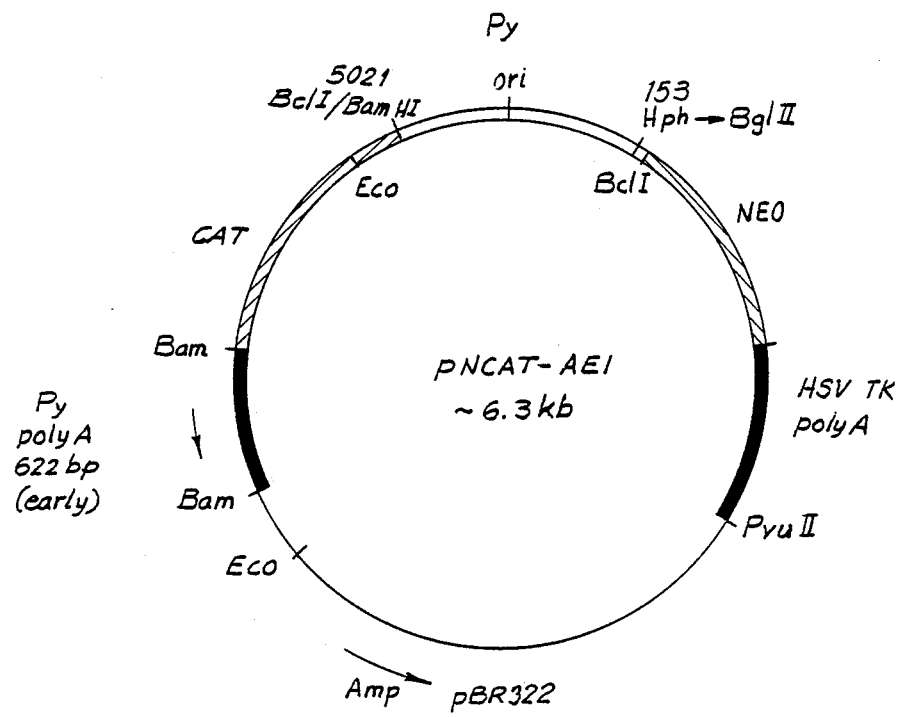

Therefore, another recombinant was constructed. This recombinat expresed CAT (chloramphenicol acetyl transferase). The plasmid used for this purpose (a derivative of pBR322) also contained a functional viral origin, a neomycin-resistance gene and the gene of interest under the control of the polyoma late promoter. This plasmid (designated pNCAT-AE1) is depicted in FIG. 4 (deposited with the American Type Culture Collection on May 16, 1985 under accession number ATCC 53127). The CAT gene was inserted at the Bcl I site starting at nucleotide 5021. In addition, the plasmid contains the polyoma origin (ori), NEO sequences contained within a Tn5 BclI/SalI fragment (hatched ares), and a HindIII-Sau3A fragment containing CAT sequences (crosshatched area) linked via BamHI linkers to the polyoma late promoter at the BclI site and followed by polyoma polyadenylation signals. The pBR322 fragment contained in this vector is indicated by the thick black line. E and L indicate the direction of early and late polyoma transcription, respectively.

As in the case of the neomycin-resistance recombinant, this plasmid should be able to integrate into the WOP genome and be excised and replicated.

To facilitate the formation of head-to-tail tandems, which in turn facilitates excision, transfection was conducted at 33° C. overnight. The transfected cells were maintained at 33° C. for a total of 24-40 hours after the addition of the calcium phosphate.

At 20 hours post-transfection, cells were plated at $1 \times 10^5$/ dish into 200 micrograms/ml of G418 sulfate (GIBCO). One set of dishes was shifted to 39° C. 24 hours post-transfection, while a second set was shifted to 39° C. 40 hours post-transfection.

At 3-4 weeks colonies were observed. The colonies were picked and assayed for extrachromosomal viral DNA replication and for CAT activity.

Before assay, the cells were shifted to a permissive temperature for varying amounts of time, preferably at least about 48 hours.

The extrachromosomal DNA replication assay was done using the Hirt procedure, supra.

The CAT activity was assayed according to the method of Gorman, C. M. et al (1982) *Mol. Cell. Biol.* 2:1044-1051 and (1982) *Proc. Natl. Acad. Sci.* (USA) 79:6777-6781, i.e. using a chloramphenicol acetyl transferase assay that measures CAT transcription from extrachromosomal templates.

Briefly, the Gorman procedure involved the following steps:

Subconfluent dishes of cells at 33° C. for 96 hours or continuously maintained at 39° C. were rinsed with phosphate buffered saline. 1 ml of 0.04M Tris-0.15M NaCl 0.001M EDTA (TNE buffer) is then added to the cells. After approximately 15 minutes the cells were scraped with a rubber policeman, agitated by pipetting to form a single cell suspension and counted with a Coulter counter. The cells were centrifuged for 2 minutes in a microfuge, the supernatant poured off and the cell pellet frozen at $-20°$ C. Approximately 100 microliters of 0.25M Tris-H Cl, pH 7.8, were added per $10^6$ cells, and the cells lysed by repeated freezing and thawing. Cell debris were centrifuged and the supernatant assayed for CAT activity. A volume of extract corresponding to that from a known number of cells was incubated with 0.15 microCurie of $^{14}$C-labeled chloramphenicol (New England Nuclear Corp.), 1M Tris-H Cl, pH 7.8, and 4 mM acetyl co-enzyme A, in a 150 microliter final reaction volume as described by Gorman, supra. The reaction was carried out at 37° C. for 20-60 minutes. Chloramphenicol was extracted with 1 ml of ethyl acetate and concentrated by evaporation. Separation of acetylated from non-acetylated forms was performed on thin layer silica gels using chloroform-methanol as a solvent, and visualized by autoradiography. The areas containing acetylated and non-acetylated forms were cut out and counted using a scintillation counter. The percent of $^{14}$C-chloramphenicol converted to acetylated forms was therefore directly related to the amount of chloramphenicol acetyl transferase enzyme present in the cell extract.

The Hirt analysis was performed using the Hirt extract from a known number of cells varying from $1 \times 10^4$ to $2 \times 10^5$ cells. The amount of amplified CAT DNA on a per cell basis was determined by comparing the intensity of hybridization to known amounts and linearized plasmid DNA.

The results indicated that shifting four different clones to 33° C. for 48 hours resulted in the production of extrachromosomal CAT DNA in all cases. Although the amount varied among the clones, one clone contained on the order of 1000 copies of CAT-containing extrachromosomal DNA per cell. Analysis of another clone indicated the extrachromosomal CAT DNA could be detected as long as 2 weeks after a shift to 33° C.

A determination of CAT enzyme levels from cells at 33° for 96 hours was in most cases consistent with the extrachromosomal CAT DNA results. All four clones tested showed an increase in CAT enzyme levels after shift to 33° C. One clone continued to have increased CAT enzyme levels after two weeks at 33° C. Another clone showed approximately a 1000 fold increase in CAT level at 33° compared to that observed at 39° C. Comparison of the amount of CAT activity to that observed with purified CAT enzyme obtained from PL Biochemicals (Milwaukee, Wisc.) having an approximate specific activity of 5000 units/mg of CAT protein indicates the CAT enzyme may constitute as much as 1% of the total cell protein in the case of the clone that undergoes the 1000 fold increase in activity after the shift to 33° C.

The method of the present invention can be used to amplify and express DNA coding for virtually any protein or protein fragment. Non-limiting examples of such proteins include lymphokines e.g. gamma-interferon and tumor necrosis factor; hormones, e.g. human growth hormone; and other biologically active substances, e.g. Factor VIII and Erythropoietin.

The WOP-32-4 cell line of the present invention is also useful in detecting the presence of origin defects in DNA. This can be done by transfecting the WOP-32-4 cells with a plasmid (that may or may not have an origin defect) as described above; obtaining the Hirt (supra) supernatant of DNA (also as described above) and digesting the DNA with Mbo I restriction endonuclease. If the DNA is digested by the enzyme, the plasmid does not contain an origin defect.

What is claimed is:

1. A method for amplifying transfected genes which comprises:
   providing a host cell transfected with a first plasmid comprising the region of virus DNA that codes for a temperature-sensitive large T antigen and a non-functional origin of replication for said virus;

transfecting said host cell with a second plasmid comprising a selectable marker gene, a functional origin of replication for said virus, and a gene directing the production of a desired protein, selecting a host cell containing said second plasmid on the basis of said selectable marker gene;

exposing and maintaining the selected host cells at a first predetermined temperature at which said cells express non-functional virus large T antigen thereby impeding replication and excision of said second plasmid; and shifting and maintaining the selected host cells to a second predetermined temperature at which said cells express functional viral large T antigen thereby inducing excision and replication of said second plasmid.

2. The method of claim 1 wherein said virus DNA comprises polyoma virus DNA.

3. The method of claim 1 which comprises growing the surviving host cells containing said selectable genetic marker in order to expand the surviving colonies.

4. The method of claim 3 wherein said first predetermined temperature is about 39° C.

5. The method of claim 4 wherein said second predetermined temperature is about 33° C.

6. The method of claim 5 wherein said maintenance of said cells at said second predetermined temperature takes place for a time period at least sufficient to permit amplification and expression of the gene for the desired protein.

7. The method of claim 6 wherein said selectable marker gene comprises a gene for neomycin resistance.

8. The method of claim 7 wherein said marker gene is dominant.

9. The method of claim 3 wherein said cell produces a non-functional large T antigen at said first predetermined temperature.

10. The method of claim 5 wherein said murine cells produce non-functional large T antigen when incubated at 39° C. and produce functional large T antigen when incubated at 33° C.

11. The method of claim 10 wherein said transfected cells comprise WOP 32-4 cells having ATCC accession number CRL8806.

12. The method of claim 7 wherein said neomycin coding sequences are linked to the polyoma late promoter and flanked on both sides by polyoma sequences to form an in virto generated partial tandem.

13. The method of claim 12 which comprises selecting neomycin resistant colonies of said cells at 39° C.

14. The method of claim 13 wherein said desired protein comprises chloramphenicol acetyl transferase.

15. The method of claim 14 wherein said desired gene comprises chloramphenicol acetyl transferase gene and said desired gene is linked to polyoma late promoter.

16. An *E coli* bacterium containing plasmid PNCAT-AE1 and deposited under accession number ATCC 53127.

17. A method for amplifyiing transferred genes by temperature induction which comprises providing a host cell transfected with a first DNA segment comprising the region of virus DNA that codes for a temperature-sensitive large T antigen and a non-functional origin of replication for said virus, introducing a second DNA comprising a selectable marker gene, a functional origin of replication for said virus, and a gene directing production of a desired protein into said host cell, and incubating said host cells at a first predetermined temperature for a predetermined time period under selective conditions and thereafter incubating selected host cells at a second predetermined temperature lower than said first predetermined temperature thereby inducing excision and replication of said second DNA.

* * * * *